United States Patent
De Smet

(10) Patent No.: US 7,209,539 B2
(45) Date of Patent: Apr. 24, 2007

(54) PROCESS AND DEVICE FOR TESTING PARTS BY X RAYS

(75) Inventor: Marie-Anne De Smet, Monbrun (FR)

(73) Assignee: Airbus France, Toulouse Cedex (FR)

( * ) Notice: Subject to any disclaimer, the term of this patent is extended or adjusted under 35 U.S.C. 154(b) by 32 days.

(21) Appl. No.: 10/379,953

(22) Filed: Mar. 4, 2003

(65) Prior Publication Data
US 2004/0037389 A1   Feb. 26, 2004

(30) Foreign Application Priority Data
Mar. 5, 2002   (FR) .................................. 02 02759

(51) Int. Cl.
*G01N 23/04*   (2006.01)
*H05G 1/64*   (2006.01)
*H05G 1/32*   (2006.01)
*H05G 1/52*   (2006.01)

(52) U.S. Cl. .................. 378/57; 378/98.7; 378/112; 378/113

(58) Field of Classification Search .................. 378/57, 378/58, 59, 98.8, 108, 110, 205, 207, 112, 378/113, 98.7
See application file for complete search history.

(56) References Cited

U.S. PATENT DOCUMENTS

| | | | |
|---|---|---|---|
| 3,835,324 A | | 9/1974 | Weigle |
| 4,803,639 A | * | 2/1989 | Steele et al. .................. 702/40 |
| 5,138,642 A | * | 8/1992 | McCroskey et al. .......... 378/19 |
| 5,638,420 A | | 6/1997 | Armistead |
| 6,333,962 B1 | | 12/2001 | Kitaguchi et al. |
| 6,507,635 B2 | * | 1/2003 | Birdwell et al. ............... 378/58 |
| 6,553,095 B2 | * | 4/2003 | Rinaldi et al. ............... 378/108 |
| 6,636,581 B2 | * | 10/2003 | Sorenson ...................... 378/58 |
| 2003/0147493 A1 | * | 8/2003 | Bueno et al. .................. 378/57 |

FOREIGN PATENT DOCUMENTS

WO   WO 01/77654 A1   10/2001

* cited by examiner

*Primary Examiner*—Edward J. Glick
*Assistant Examiner*—Irakli Kiknadze
(74) *Attorney, Agent, or Firm*—Thelen Reid Brown Raysman & Steiner LLP

(57) ABSTRACT

The non-destructive test of a structure (10) such as an aircraft fuselage is done by placing an X-ray source (16) on one side of the structure, and placing a digital camera (24) on the other side. The microcomputer (28) analyzes the image output by the digital camera in real time. If this image is unusable, at least one setting of the source (16) is modified immediately and a new acquisition is made without wasting any time. The adjustment can then be made manually or using a slaving system. The adjustment may relate to the wave length of the X-ray beam, the dose level or the pose time if the fault concerned is related to the gray level of the image. If a directional source is being used, the defect may also have an influence on the sharpness of the image and may be caused by an alignment problem.

22 Claims, 1 Drawing Sheet

PROCESS AND DEVICE FOR TESTING PARTS BY X RAYS

CROSS-REFERENCE TO RELATED APPLICATION

This application claims priority on French application No. 02 02759, entitled "Process And Device For Testing Parts By X Rays" by Marie-Anne De Smet, filed on Mar. 5, 2002.

TECHNICAL FIELD

The invention relates to a non-destructive on-site testing process for mechanical parts such as aeronautical or space structures, using the X-ray technique.

The invention also relates to a device designed to implement this process.

The process and the device according to the invention may be applied to non-destructive on-site testing of any mechanical part made from any material such as a metal, a plastic or a composite material, and particularly to large parts such as parts used on aircraft, space probes and satellites.

STATE OF THE ART

A number of inspections are carried out on aircraft structures, space probes and satellites at the time of their manufacture in order to detect the presence of cracks or the existence of any delaminations in composite materials, and to check that assembly devices such as rivets actually perform their functions correctly.

When aircraft are in operation, comparable inspections are periodically carried out on different parts of their structures, also in order to detect defects (presence of water, crack, corrosion, delamination, etc.), and if necessary to make the appropriate repairs.

In particular, one of the non-destructive testing methods used for this purpose is the X-ray testing technique.

According to this technique, an X-ray generating source is placed on one side of the part to be tested and films sensitive to X-rays are placed on the other side of the said part. More precisely, a directional source is usually used that may for example be placed inside an aircraft fuselage, approximately at the center of the fuselage, and that is oriented radially towards the fuselage wall. A series of films sensitive to X-rays is also placed on the outside surface of the said wall, over the entire area to be tested. This is done using an adhesive tape that will fix the films on the wall of the fuselage.

The X-ray generating source is chosen and adjusted as a function of the expected characteristics of the part to be tested. This choice applies to the radiation wave length (usually expressed in kV) and the quantity of rays emitted, or the "dose level" usually expressed in mA).

When the source is put into operation, in other words during the "firing" period, all persons present must be evacuated outside a safety perimeter, the area on which depends on the dose level emitted by the source. Firing is usually done at night in order to limit risks.

A series of firings is carried out to test a given area, modifying the orientation of the source between two successive firings. The duration of each firing is usually between two and five minutes, to enable exposure of the detector film on the other side of the part to the X-rays. This time is multiplied by the number of successive firings necessary to test the area considered.

When the series of firings is finished, the films are removed and taken to the development site, to develop each of them in turn. The results thus obtained then have to be interpreted. In practice, all these operations in addition to the firings themselves usually make it necessary to immobilize the aircraft or the structure tested during a complete night.

It frequently happens (approximately once in every two cases) that the results obtained after development of the films show that the initial setting of the source was not adapted to the structure being tested, or that the films moved during exposure to the X-rays. In this case, all the operations that have just been described have to be repeated. This doubles the time during which the aircraft or any other structure tested by this process is immobilized.

When such an X-ray testing technique is applied to aircraft maintenance, it often results in the simultaneous immobilization of several aircraft located in the same hangar as the aircraft being tested, within the safety parameter. If the immobilization time is doubled because the test has to be restarted, then there is a large prejudice for the airline company(ies) concerned.

Furthermore, "traceability" requirements apply to airline companies to keep the films obtained during successive tests carried out on each aircraft for 10 to 30 years. This becomes a very expensive management procedure for a company with a large fleet.

The problem of storing unused films also induces a difficult management procedure; these films must be kept under very strict temperature and humidity conditions to prevent degradation of their technical characteristics.

When a film is defective (manufacturing defect, loss of its technical characteristics, etc.) it is impossible to perceive that it is defective other than by developing the film, in other words after it has been used for firing which makes it necessary to repeat the firing.

If a previously used film is accidentally stored with blank films, the only way to know this isn't a defect is to develop the film after it has been used during firing.

Another known method for using non-destructive testing techniques based on X-rays, is to replace the directional source by a panoramic source that emits X-rays in the entire tested area, without it being necessary to modify the orientation between two successive firings.

However, this type of panoramic source is rarely used due to its cost. Furthermore, such a source cannot solve the problems related to the use of films.

PRESENTATION OF THE INVENTION

The main purpose of the invention is to propose a process and a device with a new design to solve at least some of the problems caused by processes and devices according to prior art using X-ray detection films.

More precisely, the purpose of the invention is to propose a process and a device to considerably reduce the immobilization time of the tested structure and to simplify the procedure for acquisition, processing and storage of the data thus obtained.

According to the invention, this result is obtained by use of a process for non-destructive testing of a structure, according to which a first image acquisition step is executed consisting of emitting an X-ray beam using an X-ray emitting source placed adjacent to the structure and detecting the said beam on the other side of the structure, so as to obtain an image of the said structure through which the X-rays pass, characterized in that the said beam is detected using a digital camera detecting X-rays, the image of the structure output by the digital camera is analyzed in real time in order to determine whether or not this image is useable, and if it is determined that the image is unusable, then at least one of the settings of the said source is modified and a new image acquisition step and a new image analysis are carried out in real time.

The use of a digital camera detecting X-rays to detect the beam on the other side of the structure to be tested also provides an image of the said structure in real time. It is thus possible to determine immediately whether or not the image can be used. If not, the setting(s) that is(are) shown to be defective by the image output by the digital camera (the settings may be defective because the structure to be tested is not the same as the structure that should theoretically have been tested) and a new image acquisition step and a new image analysis step are then carried out in real time. This results in a very large time saving, particularly if the initial settings were not good, which is what happens on average in about one testing operation out of two. When the test concerns aircraft, it can be understood that this time saving provides a considerable advantage for airline companies owning the immobilized aircraft.

Furthermore, the necessary dose if a digital camera is used is lower than the dose required for the use of a film. Consequently, the surface area of the safety perimeter during the firing period can be reduced.

Furthermore, due to its compactness, a digital camera may be slid into locations that would previously have required disassembly of the structure with the use of films.

Quality indicators such as different diameter wires are used to determine whether or not an image is useable, in real time. These indicators may be fixed to one side of the camera objective to enable a continuous setting.

According to a first aspect of the invention, it is determined that the image is unusable when at least one of the magnitudes consisting of the grey level and the sharpness of the image is not sufficient to determine any defects being searched for in the structure being tested to be detected.

When the grey level of the image is not sufficient to detect any defects being searched for in the said structure, at least one of the settings of the source consisting of the wave length of the X-ray beam, the dose level and the exposure time, is modified.

In a first embodiment of the invention, a directional source is used. In this case, when the sharpness of the image is not sufficient to detect any defects being searched for in the said structure, the orientation of the source is modified.

If it is determined that the image cannot be used, then a manual adjustment of the source is made. However, according to a preferred embodiment of the invention, at least one adjustment of the source can be modified automatically, in real time.

According to the first embodiment of the invention, a directional source is used and the source and the digital camera are moved simultaneously and automatically along a predetermined path, so as to scan an area of the said structure to be tested. In this case, the detector may be slaved to the source, or the source may be slaved to the detector.

According to a second embodiment of the invention, a panoramic source is used and the digital camera is automatically moved along a predetermined path, so as to scan an area of the said structure to be tested.

Another purpose of the invention is a device for non-destructive testing of a structure, comprising an X-ray emitting source that may be placed on one side of the structure and emitting an X-ray beam, means of detection of the said beam that can be placed on the other side of the structure so as to obtain an image of the structure through which the X-rays pass, characterized in that the detection means comprise a digital camera that detects the X-rays, the testing device also comprising means of analyzing the image of the structure output by the digital camera in real time, in order to determine whether or not this image is useable, and means of modifying at least one setting of the source, if it is determined that the image is unusable.

BRIEF DESCRIPTION OF THE DRAWINGS

We will now describe two preferred embodiments of the invention for illustrative purposes and in no way restrictive, with reference to the attached drawings, wherein.

DETAILED PRESENTATION OF PREFERRED
EMBODIMENTS OF THE INVENTION

Figure 1:
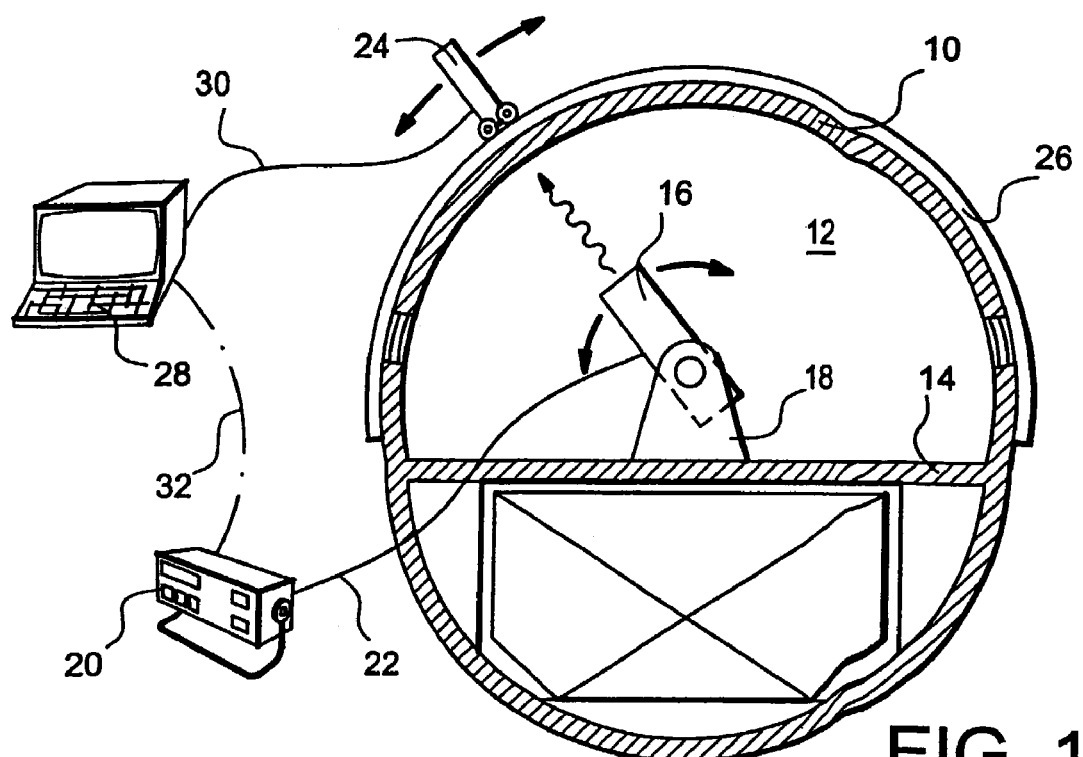
FIG. 1 is a partial sectional view diagrammatically illustrating a non-destructive testing device using a directional source according to a first embodiment of the invention, applied to testing an area of the fuselage of an aircraft.
Figure 2:
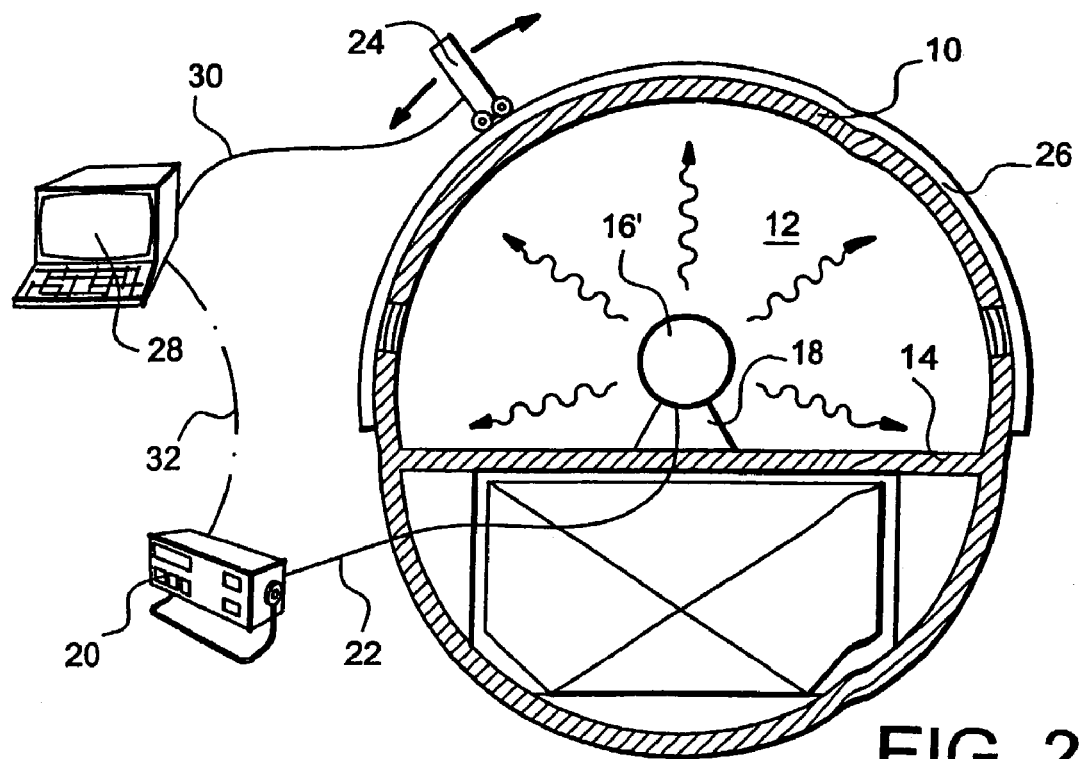
FIG. 2 is a partial sectional view comparable to that in FIG. 1, diagrammatically illustrating a non-destructive testing device using a panoramic source according to a second embodiment of the invention, applied to testing an area of the fuselage of an aircraft.

FIGS. 1 and 2 illustrate two embodiments of a non-destructive testing device using X-rays according to the invention. In both cases, the device is used to test a determined area of an aircraft fuselage. However this application only forms one example of a use of the process according to the invention. The device according to the invention may be used in all cases in which it is desired to test a structure with relatively large dimensions using X-rays in the shortest possible time and without it being necessary to restart this operation several times. Thus, possible applications of the invention apply equally well to structures being made and to existing structures in the aeronautics, space, shipping, railway fields, etc.

In FIGS. 1 and 2, reference 10 denotes an aircraft fuselage, in which a determined area, in this case delimiting the cabin 12 of the aircraft, is to be subjected to a non-destructive structural test using X-rays.

In the embodiment illustrated in FIG. 1, a directional X-ray emitting source 16 is placed on the floor 14 of the cabin 12. More precisely, the source 16 is installed on the floor 14 on a support 18. The support 18 is equipped with means (not shown) for modifying the orientation of the source 16 in a controlled manner, as diagrammatically illustrated by the arrows.

The source 16 may be composed of any X-ray generator capable of emitting a divergent beam of X-rays at a usually variable wave length and dose level. The exposure time, which corresponds to the beam emission duration, is also adjustable.

The adjustments of the source 16 are made using a testing unit 20 that an operator uses to display the required characteristics. The testing unit 20 is placed outside the safety perimeter that must be formed around the source 16 when the firing is done. Consequently, the testing unit 20 is placed outside the aircraft and is connected to the source 16 by a cable 22. As a variant or in a complementary manner, a wireless connection, for example a radio link, may also be provided between the testing unit and the X-ray source.

With the arrangement that has just been described, an operator can adjust the wave length, the dose level and the exposure time of the X-ray beam being output by the source from a remote position, and then control each firing of the source, using the testing unit 20.

This arrangement also enables an operator to modify the orientation of the source 16 from a remote location, by controlling its displacement on its support 18 using the testing unit 20.

According to the invention, the non-destructive testing device illustrated in FIG. 1 also comprises detection means consisting of a digital camera 24 designed to be placed outside the fuselage 10 along the extended line of the beam of X-rays emitted by the source 16.

The digital camera 24 comprises a scintillator, in other words a transparent luminescent screen, that the incident X-rays collide into after they have passed through the wall of the fuselage 10. Inside the camera, an optic composed of a reduced diffraction magnifying objective directs the light beam output from the scintillator onto a CCD diode matrix that transforms this light beam into electric signals. In other words, the digital camera 24 outputs electric signals in real time representing the image of the region of the wall of the fuselage through which the X-ray beam emitted by the source 16 passes.

In the embodiment diagrammatically illustrated in FIG. 1, the digital camera 24 is mounted on the outside surface of the area of the fuselage 10 to be tested, for example using one or several rails 26. More precisely, the digital camera 24 moves along the rails 26 around the entire circumferential area of the fuselage 10 to be tested. If necessary, a mechanism (not shown) moves the camera 24 along a direction parallel to the longitudinal axis of the fuselage with respect to the rails 26. Motor drive means (not shown) are associated with this assembly to move the digital camera 24 along the rails 26 and any other associated mechanism. This displacement is diagrammatically illustrated by the arrows in FIG. 1.

The electric signals output by the digital camera 24 representative of the image of the region of the wall of the fuselage through which the X-ray beam passes, are transmitted to means capable of analyzing this image in real time. These analysis means are materialized by a microcomputer 28.

Like the testing unit 20, the microcomputer 28 must be placed outside the safety perimeter provided around the X-ray source 16, so that it can be used without any risk by operators. Therefore, the microcomputer 28 is located outside the aircraft being tested.

The connection between the microcomputer 28 and the digital camera 24 is made through a cable 30. As a variant, the microcomputer 28 may also be connected to the digital camera 24 through a wireless link such as a radio link. These two link types may also be used simultaneously.

Note that the motors (not shown) used to displace the digital camera 24 along the rails 26 and on any other associated mechanism are also remote controlled from the outside of the safety perimeter. This remote control is advantageously coupled to the remote control that modifies the orientation of the X-ray source 16, to keep the digital camera 24 aligned with the source 16 when the camera is moved. As already mentioned, this control is made, for example from the testing unit 20, through a connecting cable. However, any other arrangement would be possible without departing from the scope of the invention.

When the testing device conform with the invention is used to test an open structure, for example such as an aircraft wing element, the X-ray source 16 and the digital camera 24 may be directly connected to each other by a rigid mechanism overlapping this structure.

The use of the testing device that has been described with reference to FIG. 1 will now be explained.

In a first step, when the source 16 and the digital camera 24 are not mechanically connected to each other, they are aligned according to a first firing line among a set of firing lines corresponding to the overall area to be tested. Consequently, different means may be used for this purpose, such as orientation and position marks arranged on the support 18 and rails 26, sights, etc.

The X-ray source is also adjusted taking account of the expected characteristics of the tested structure, in accordance with the usual practice. This adjustment concerns the wave length of the X-ray beam emitted by the source, the dose level (in other words the power of the beam) and the exposure time.

When the adjustments are finished, a first firing is made. Thus, this gives an image of the structure between the source 16 and the digital camera 24, in real time. Starting from this image which is instantaneously displayed on the microcomputer 28, it is possible to know almost instantaneously whether or not the image is useable. This judgment may be made either by an operator who observes the image displayed on the screen of the microcomputer 28, or using an appropriate software that processes the signals from the digital camera 24 directly.

The nature (useable or unusable) of the image output by the digital camera 24 is determined firstly as a function of the grey level in this image, and secondly as a function of its sharpness.

When the grey level is not sufficient for the image output by the digital camera to be usable, this means that at least one of the settings of the X-ray source 16 is not satisfactory and must be modified, as a person skilled in the subject is well aware. The wave length of the X-ray beam, the dose level and/or the exposure time thus have to be modified, to give an image with a satisfactory grey level.

According to the invention, this information is immediately available and is applied either to make a manual modification of the settings of the source on the testing unit 20, or by a slaving system that directly modifies the settings by acting on the said testing unit through a link symbolized by the chain dotted line 32 in FIG. 1.

The image instantaneously output by the X-ray source 16 may be unusable due to a sharpness fault, and as a person skilled in the subject is well aware, this can happen particularly because the alignment of the digital camera 24 and the source is poor, or if there are vibrations, or if the dose level is insufficient.

According to the invention, this information is also available directly and is taken into account. In the same way as for a defect concerning the grey level, this information can be used manually or by appropriate slaving, by acting on at least one of the motors to orient the source 16 on its support 18 and to move the digital camera 24 on the rails 26 or on an associated mechanism, if any.

The invention can thus be used to obtain a useable image of the tested area of the structure, in a well determined manner, in a very short time when the correction is made manually, and almost instantaneously when a slaving system is used.

Furthermore, due to the fact that the image of the tested area is digitized by the camera 24, this image may be stored particularly easily on any type of support, and particularly on conventional computer supports, for a very long period without any particular constraints. One particular result is a very significant reduction of the volume necessary to archive images and improve traceability, compared with conventional X-ray testing techniques using detection means consisting of photographic films.

When a first firing has been made and it is found that adjustments have to be made to the source and/or the alignment between the source and the digital camera, a second firing is carried out to acquire a useable image that can be used to detect defects in the structure such as cracks, voids, porosity, delamination, etc.

A test of the entire area concerned by the operation is then carried out, scanning this area by joint displacement of the source 16 and the digital camera 24. More precisely, these two units are displaced step by step around a predetermined path to test the entire area concerned. This displacement is preferably made automatically, under the control of software that acts on motors that pivot the source 16 on its support 18 and move the digital camera 24 along the rails 26, and possibly on the associated mechanism. However, as a variant, this could be done manually without departing from the scope of the invention.

A new firing is done each time that the assembly consisting of the source 16 and the camera 24 is stopped. The result is a sequence of digitized images, which as a whole represents the entire tested area.

The above description shows that the process and the device according to the invention can be used to test a large mechanical structure in a much shorter time than would be possible with existing processes and devices using detection means consisting of photographic films. The real time analysis of the image output by the digital camera enables almost immediate modification of the settings of the source and the source—digital camera alignment during the first firing without any development. Furthermore, acquisition of an image using the digital camera is significantly faster than using a photographic film.

The second embodiment of the invention illustrated in FIG. 2 differs from the first embodiment essentially by the fact that the directional source 16 is replaced by a panoramic source 16', installed in a fixed manner on the support 18. All other characteristics of the device are unchanged.

In general, the use of the testing device illustrated in FIG. 2 is comparable to that of the device in FIG. 1. The only difference is due to the fact that the source 16' is panoramic and fixed. It emits an X-ray beam that scans the entire area of the fuselage 10 to be tested. Consequently, only the digital camera is moved step by step along a predetermined path during the image acquisition step.

This embodiment automatically eliminates any alignment problem. In this case, the real time analysis of the first image obtained and any setting changes made subsequently according to the invention are only applicable to the wave length of the X-ray beam, the dose level and the exposure time.

Obviously, the invention is not limited to the embodiment that has just been described as an example. In particular, and as already mentioned, the testing process and device according to the invention may be used to test any large structure, regardless of the nature of the said structure and regardless of the nature of the material(s) from which it is composed. If the detector and the source are both mobile, the detector may be slaved to the source, as is described with reference to FIG. 1, or the source may be slaved to the detector. Finally, in the case of a closed structure such as an aircraft fuselage, the arrangement may be inverted, in other words the detector may then be placed inside the structure and the source outside the said structure.

I claim:

1. Process for non-destructive on-site testing of a large mechanical industrial structure, wherein a first image acquisition step comprises:
   placing an X-ray emitting source on one side of the large industrial structure;
   emitting an X-ray beam from the X-ray emitting source;
   detecting the beam on the other side of the industrial structure using a digital camera detecting X-rays, so as to obtain an image of the industrial structure through which the X-rays pass, the digital camera including a scintillator, a CCD diode matrix, and an optics provided between the scintillator and the CCD diode matrix, the optics directing a light beam output from the scintillator onto the CCD diode matrix;
   analyzing, in real time, the obtained image of the industrial structure output from the digital camera in order to determine whether or not the obtained image is usable; and
   if it is determined that the obtained image is unusable, automatically and directly modifying the setting of the X-ray emitting source and carrying out, in real time, a new image acquisition step for the industrial structure by repeating said emitting, said detecting, and said analyzing.

2. Process according to claim 1, wherein it is determined that the obtained image is unusable when at least one of the magnitudes consisting of the grey level and the sharpness of the image is not sufficient to detect any defects being searched for in the said structure.

3. Process according to claim 2, wherein when the grey level of the obtained image is not sufficient to detect any defects being searched for in the said structure, at least one of the settings of the source consisting of the wave length of the X-ray beam, the dose level and the exposure time, is modified.

4. Process according to claim 2, wherein a directional source is used and, when the sharpness of the obtained image is not sufficient to detect any defects being searched for in the structure, the orientation of the source is modified.

5. Process according to claim 1, wherein a directional source is used and the source and the digital camera are displaced simultaneously and automatically along a predetermined path, so as to scan an area of the said structure to be tested.

6. Process according to claim 1, wherein a panoramic source is used and the digital camera is automatically moved along a predetermined path, so as to scan an area of the said structure to be tested.

7. Process according to claim 1, further comprising:
   acquiring successive usable images of the industrial structure, by moving the digital camera along a predetermined path and repeating said emitting, said detecting, said analyzing, and, if necessary, said modifying.

8. Process according to claim 1, wherein said placing includes:
   installing the X-ray emitting source inside the industrial structure, the digital camera detecting the beam outside the industrial structure.

9. Process according to claim 1, wherein said analyzing includes:
   automatically determining whether or not the obtained image is usable as a function of the gray level of the obtained image and a function of the sharpness of the obtained image.

10. Device for non-destructive on-site testing of a large mechanical industrial structure, said device comprising:

an X-ray emitting source adapted to be placed on one side of the large industrial structure and to emit an X-ray beam;

means for detecting the X-ray beam, said means for detecting adapted to be placed on the other side of the structure so as to obtain an image of the industrial structure through which the X-rays pass, said detection means comprising a digital camera that detects the X-rays, the digital camera including a scintillator, a CCD diode matrix and an optics provided between the scintillator and the CCD diode matrix, the optics directing a light beam output from the scintillator onto the CCD diode matrix;

means for analyzing, in real time, the obtained image of the industrial structure output from the digital camera in order to determine whether or not the obtained image is usable; and means for automatically modifying at least one setting of the source, if it is determined that the obtained image is unusable, said means for modifying acting directly on the source in real time.

11. Device according to claim 10, wherein said means for analyzing determines that the image is unusable when at least one of the magnitudes consisting of the grey level and the sharpness of the image is not sufficient to detect any defects being searched for in the said structure.

12. Device according to claim 11, wherein when the grey level of the image is not sufficient to detect any defects being searched for in the structure, said means for modifying adjusts at least one of the settings of the source consisting of the wave length of the X-ray beam, the dose level and the exposure time.

13. Device according to claim 11, wherein the source is directional, and when the sharpness of the image is not sufficient to detect any defects being searched for in the said structure, said means for modifying adjusts at least one of the settings of the source so as to modify the orientation of the source.

14. Device according to claim 10, wherein the X-ray emitting source is a directional source, said device further comprising:

means for simultaneously and automatically displacing the source and the digital camera along a predetermined path, so as to scan an area of the said structure to be tested.

15. Device according to claim 10, wherein said X-ray emitting source is a panoramic source, said device further comprising:

means for automatically moving the digital camera along a predetermined path, so as to scan an area of the said structure to be tested.

16. Device according to claim 10, further comprising:

means for moving said digital camera along a predetermined path such that successive usable images of the industrial structure are obtained at locations along the predetermined path.

17. Device according to claim 10, wherein said X-ray emitting source is further adapted to be installed inside the industrial structure, said digital camera detecting the beam outside the industrial structure.

18. Device according to claim 10, wherein said means for analyzing automatically determines whether or not the obtained image is usable as a function of the gray level of the obtained image and a function of the sharpness of the obtained image.

19. Process for non-destructive on-site testing of a large mechanical industrial structure, wherein a first image acquisition step comprises:

emitting an X-ray beam using a fixed panoramic X-ray emitting source placed on one side of the large industrial structure in order to scan an entire area of the industrial structure to be tested;

detecting the X-ray beam on the other side of the structure using a digital camera detecting X-rays, so as to obtain, at locations along a predetermined path, an image of the industrial structure through which the X-rays pass, by moving step by step the digital camera along the predetermined path, the digital camera including a scintillator, a CCD diode matrix, and an optics provided between the scintillator and the CCD diode matrix, the optics directing a light beam output from the scintillator onto the CCD diode matrix;

analyzing, in real time, the obtained image of the industrial structure output from the digital camera at respective locations along the predetermined path, in order to determine whether or not the obtained image is useable; and if it is determined that the obtained image is unusable, automatically and directly modifying the setting of the source and carrying out, in real time, a new image acquisition step for the industrial structure by repeating said emitting, said detecting, and said analyzing.

20. Process according to claim 19, wherein said analyzing includes:

automatically determining whether or not the obtained image is usable as a function of the gray level of the obtained image and a function of the sharpness of the obtained image.

21. Device for non-destructive on-site testing of a large mechanical industrial structure, said device comprising:

a fixed panoramic X-ray emitting source adapted to be placed on one side of the large structure and to emit an X-ray beam so as to scan an entire area of the industrial structure to be tested;

means for detecting the beam adapted to be placed on the other side of the industrial structure so as to obtain, at locations along a predetermined path, an image of the industrial structure through which the X-rays pass, said detection means comprising a digital camera that detects the X-rays, the digital camera including a scintillator, a CCD diode matrix, and an optics provided between the scintillator and the CCD diode matrix, the optics directing a light beam output from the scintillator onto the CCD diode matrix;

means for moving the digital camera step by step along the predetermined path;

means for analyzing, in real time, the obtained image of the structure output from the digital camera at respective locations along the predetermined path, in order to determine whether or not the obtained image is useable; and means for automatically modifying at least one setting of the source, if it is determined that the obtained image is unusable, said means for modifying acting directly on the source in real time.

22. Device according to claim 20, wherein said means for analyzing automatically determines whether or not the obtained image is usable as a function of the gray level of the obtained image and a function of the sharpness of the obtained image.

* * * * *